(12) United States Patent
Betts-Lacroix et al.

(10) Patent No.: US 10,274,433 B1
(45) Date of Patent: Apr. 30, 2019

(54) DEVICE AND METHOD OF MEASURING ANIMAL HEALTH

(71) Applicant: Vium, Inc., San Mateo, CA (US)

(72) Inventors: Jonathan Betts-Lacroix, Belmont, CA (US); Laura R. Schaevitz, Los Gatos, CA (US); Kyle Howard Heath, Menlo Park, CA (US)

(73) Assignee: Vium, Inc., San Mateo, CA (US)

( * ) Notice: Subject to any disclaimer, the term of this patent is extended or adjusted under 35 U.S.C. 154(b) by 396 days.

(21) Appl. No.: 14/872,060

(22) Filed: Sep. 30, 2015

(51) Int. Cl.
*G01N 21/78* (2006.01)
*G01N 21/77* (2006.01)
*G01N 21/75* (2006.01)

(52) U.S. Cl.
CPC ....... *G01N 21/78* (2013.01); *G01N 2021/752* (2013.01); *G01N 2021/7759* (2013.01); *G01N 2021/7793* (2013.01)

(58) Field of Classification Search
CPC ............. G01N 21/78; G01N 2021/752; G01N 2021/7793; G01N 2021/7759
See application file for complete search history.

(56) References Cited

U.S. PATENT DOCUMENTS

| | | |
|---|---|---|
| 4,869,206 A | 9/1989 | Spina |
| 5,559,036 A | 9/1996 | Mienie et al. |
| 5,596,948 A | 1/1997 | Ritchie |
| 6,001,658 A | 12/1999 | Fredrickson |
| 8,481,330 B2 | 7/2013 | Matsuda et al. |
| 8,506,902 B2 * | 8/2013 | Rakow ................... G01N 21/78 422/421 |
| 8,968,198 B2 | 3/2015 | Brauker et al. |
| 2007/0092975 A1 * | 4/2007 | Potyrailo .......... B01L 3/502715 436/169 |
| 2009/0187392 A1 | 7/2009 | Riskey et al. |
| 2009/0253219 A1 | 10/2009 | Bauer et al. |

(Continued)

FOREIGN PATENT DOCUMENTS

| | | |
|---|---|---|
| EP | 2440039 A2 | 6/2010 |
| WO | WO2011008682 A1 | 1/2011 |
| WO | WO2013170129 A1 | 11/2013 |

OTHER PUBLICATIONS

Kim, Samuel; Transforming Plastic Surfaces with Electrophilic Backbones from Hydrophobic to Hydrophilic; ACS Applied Materials & Interfaces; acsami.org; Jan. 7, 2015; 7 pages.

(Continued)

*Primary Examiner* — Samuel P Siefke
(74) *Attorney, Agent, or Firm* — Kim Rubin

(57) ABSTRACT

A test pad comprising multiple test patches and urine detection patches in an array is described. The test pad is suitable for automated urine analysis of multiple animals in a cage. Urine detection patches may be arranged in a BAYER pattern or as rings. Multiple layers, including a substrate, a wicking layer, a test patch layer, and optional protection layer serve to manage puddles of urine. Various isolation elements are described that keep urine puddles from spreading. Color reference spots on the pad are used for dynamic color determination of test patches. Urine detection patches start a read clock and identify which test patches are valid. Elements to hold and align the test pad are described. Methods of detection and reading are described.

7 Claims, 9 Drawing Sheets

(56) References Cited

U.S. PATENT DOCUMENTS

| | | | |
|---|---|---|---|
| 2011/0123395 A1* | 5/2011 | Lambert | A61F 2/34 422/28 |
| 2012/0106811 A1* | 5/2012 | Chen | A61B 10/007 382/128 |
| 2012/0137758 A1 | 6/2012 | Mizumachi et al. | |
| 2012/0165626 A1* | 6/2012 | Irina | A61B 5/14517 600/316 |
| 2012/0180731 A1 | 7/2012 | Garner et al. | |
| 2012/0198684 A1* | 8/2012 | Carrilho | B01L 3/502707 29/527.1 |
| 2013/0034869 A1* | 2/2013 | Whitesides | B01L 3/502738 435/7.92 |
| 2013/0089858 A1* | 4/2013 | Wong, Jr. | G01N 33/54386 435/6.1 |
| 2013/0230870 A1 | 9/2013 | Barasch et al. | |
| 2014/0051173 A1* | 2/2014 | Barstis | G01N 21/78 436/43 |
| 2015/0017733 A1 | 1/2015 | Larson et al. | |
| 2016/0057413 A1* | 2/2016 | Zhou | H04N 17/02 348/135 |

OTHER PUBLICATIONS

Rats under a black light; http://www.ratbehavior.org/BlackLight.htm.

Wu, LX; A combined solid phase extraction/capillary gel electrophoresis method; Beijing Institute of Radiation Medicine, Beijing 100850, PR, China; Nov. 30, 2008; abstract.

Junhua, L; Development of an ICA strip for the rapid detection of phenylethanolamine A; Biology Inst. of Hebei Academy of Sciences, 050051, PR, China; Mar. 15, 2015; abstract.

Nikolaeva, TL; The development and application of an immunoenzyme assay kit; http://www.ncbi.nlm.nih.gov/pubmed/19172894; 2008-12-0; abstract.

Cybow Urinalysis Reagent Test Strips 11 Parameter; images of a publicly traded product; taken Sep. 26, 2015.

* cited by examiner

DEVICE AND METHOD OF MEASURING ANIMAL HEALTH

FIELD OF THE INVENTION

The invention relates to automated measurement of animal health, in particular via urine analysis, in particular automated urine analysis of animals in a vivarium.

BACKGROUND

Vivariums house a number of animals, typically test animals, such as mice or other rodents, in a number of cages, often a large number. The test animals are frequently used to test drugs, genetics, animal strains, husbandry experiments, methods of treatment, procedures, diagnostics, and the like. We refer to all such uses of a vivarium as a study.

The prior art of vivariums is labor-intensive. The animals must be monitored for behavior and health. This is typically done by direct observation, or by removing an animal from its cage for more careful inspection and tests.

Such manual observations and measurements are inherently infrequent, such as once per day per animal. This infrequency creates three weakness of the prior art. First, problems such as sickness may not be discovered until after an unacceptable delay. Second, subtle health changes will be missed. Third, such observation and out-of-cage testing require light for the observer. For the convenience of the vivarium operation, most animal tests are done in light, during the day. The natural activity period of mice is at night, in the dark. This timing not only misses health issues that happen during their normal activity period, but also puts stress on the animals, as the light interferes with and alters their normal behavior and health, and thus alters the results of the study compared with animals in their natural lighting regimen.

Prior art includes urine test strips. A typical paper strip comprises ten to twelve small treated squares, or patches. When the strip is saturated with urine, each square changes color based on one particular attribute of the urine. The colors of the patches are read manually, comparing each square against a set of reference colors to determine the best match. The patches on the strip must be read at a specified time from saturation, such as one minute. Often, different patches require a different read time.

Such strips are not well suited for measuring mice urine in a cage. A puddle of urine is likely not fresh, and may well be contaminated. In addition, if there are multiple mice in a cage, which is common, it is unlikely that a determination can be made of which mouse produced the urine. Alternatively, placing a mouse in a clean sanitary enclosure to collect its urine, separate from its home cage, is very labor intensive and stresses the mouse, as discussed above.

Prior art does not include any method of fully automated urine analysis of multiple mice in a home cage on a continual basis.

SUMMARY OF THE INVENTION

We discuss mice as prototypical animals in this specification, and in claims and drawings. However, embodiments of this invention are equally applicable to other rodents and other animals. All descriptions and claims directed to mice are also directed to rodents and also directed to animals in general.

One non-limiting exemplary embodiment of a device, and one exemplary non-limiting scenario of use and benefit is described below.

A vivarium mouse cage has five mice. A pad of this invention is placed in the cage, positioned accurately via the use of holes in the pad and pins on the floor of the cage. An adhesive strip secures the pad to the bottom of the cage. The precise positioning is needed so the two cameras, one IR and one color, and responsive video analytic software, know where the pad is, and know where the elements in the pad are. Also, mice like to push objects around in their cage, as well as chew on everything.

The pad comprises numerous test patches that measure, via color change, various attributes of urine. It also comprises color reference patches, to which the test patches are compared, using video camera(s) and responsive software.

The normal activity period for mice is in the dark, so the cage is illuminated by and video monitored with IR. When a mouse is over the pad and urinates, urine or moisture sensors in the pad rapidly change color, which is detected by the IR camera and corresponding software. This triggers the start of a timer. After the timer expires, say in one minute, the pad is read by either the IR camera or, after turning on white LEDs focused only on the test pad, the color camera.

First, the urine detection patches are read to determine the extent of the fresh urine. Test patches completely surrounded by positive urine detection patches are assumed to provide valid test results. Test patches completely surrounded by negative urine detection patches are assumed to be unused and may be used for future tests. Test patches surrounded by some positive and some negative urine detection patches may be both invalid for the current urine sample, and also not usable for future urine samples. However, for some tests, that test patch may be currently usable and may be usable for future tests. Computer software tracks the state of test patches and urine detection patches. The color reference patches are used for comparison of currently valid test patches to determine a corresponding attribute of the fresh urine.

An alternative or supplement to urine detection patches is the use of an ultra-violet (UV) light source. Because urine glows under UV, a camera, either an IR camera or a color camera, detects fresh urine anywhere on the pad. By comparing the location(s) of prior urine to the current location(s) of urine the determination of fresh urine is made. The UV light may be directional, directed to only the pad and turned on only when no animal is on the pad so that the animal is not exposed to UV light. The addition of the UV light source is explicitly claimed for both device and method embodiments. The use of UV light to detect urine is explicitly claimed as an alternative to, and also in addition to, urine detection patches. The detection of fresh urine by the methods of this paragraph is explicitly claimed as method steps.

The pad is comprised of layers. One layer comprises the test patches. Above or below the test patches is a wicking layer designed to distribute urine to multiple test patches. If the wicking layer is above the test patches it is either transparent, translucent, or has viewing holes through which the test patches are read. Below the pad is a substrate layer that provide both mechanical strength and prevents urine from leaking through. At the top surface of the pad is a protection layer, which is ideally transparent plastic with small holes through which urine will penetrate to the test patch layer and the wicking layer. Some layers may be combined, and some layers are options.

This ideal, exemplary test patch comprises color reference patches that are used for matching test patches and thus reading the currently valid test patches. The color reference patches may be raised or may be under a portion of the protection layer that is free of holes, so that urine does not contaminate the color reference patches.

This ideal, exemplary test patch has urine blocking lines, walls or ridges whose purpose is to contain a puddle of urine so that it does not wet test patches or urine detection patches outside of a defined, determinable urine puddle region. These urine-blocking lines may be gaps or solid regions of the wicking layer. They may be ridges formed in any of the layers. They may be created by yet another layer. The wicking layer may be melted to form the lines or the substrate layer formed to create ridges. The wicking layer may be integrated with the test patch layer, for example paper on which the test patches are applied or printed. In such embodiments, gaps or non-wicking portion in this layer are required to minimize urine puddle spread.

This ideal, exemplary test patch may comprise lines or targets to aid in video image alignment, aid in homography image correction, and aid in locating detritus, such as bedding, on top of the pad.

Since the cage has multiple mice, it is necessary to identify which mouse urinated to associate that mouse with the test results from the pad. That mouse may be identified before, during or after urination. Mice may be identified by tail markings, RFID, or other means novel or known in the art. The mice in the cage are tracked via the camera(s) and video analytics in order to associate the correct mouse with the urination test results, particularly if the location in the cage or the location in time is different that then location and time of urination.

Mice do not like white light during their dark diurnal period. Thus, in our exemplary scenario, after the urination, the mouse then moves to a different portion of the cage, possibly inside a mouse house. Then, the pad may be read by directional white light and the use of color camera. If the mouse fails to move sufficiently far away, so that it will not be exposed to white light, then the white light is not turned on and there may be no test results from that urination. A mouse may be encourage to move in the cage by the use of heat, light, noise, food, motion, scent or other stimulus. Note that the IR and the color camera may be the same or different cameras, or one camera that is configurable.

When the test pad is used up to a threshold of remaining unused test patches, notification is provided to a human attendant to replace the used pad with a fresh pad.

Pads may be coded with a unique machine-readable or human-readable (or both) serial number or equivalent.

DETAILED DESCRIPTION

Figure 1:
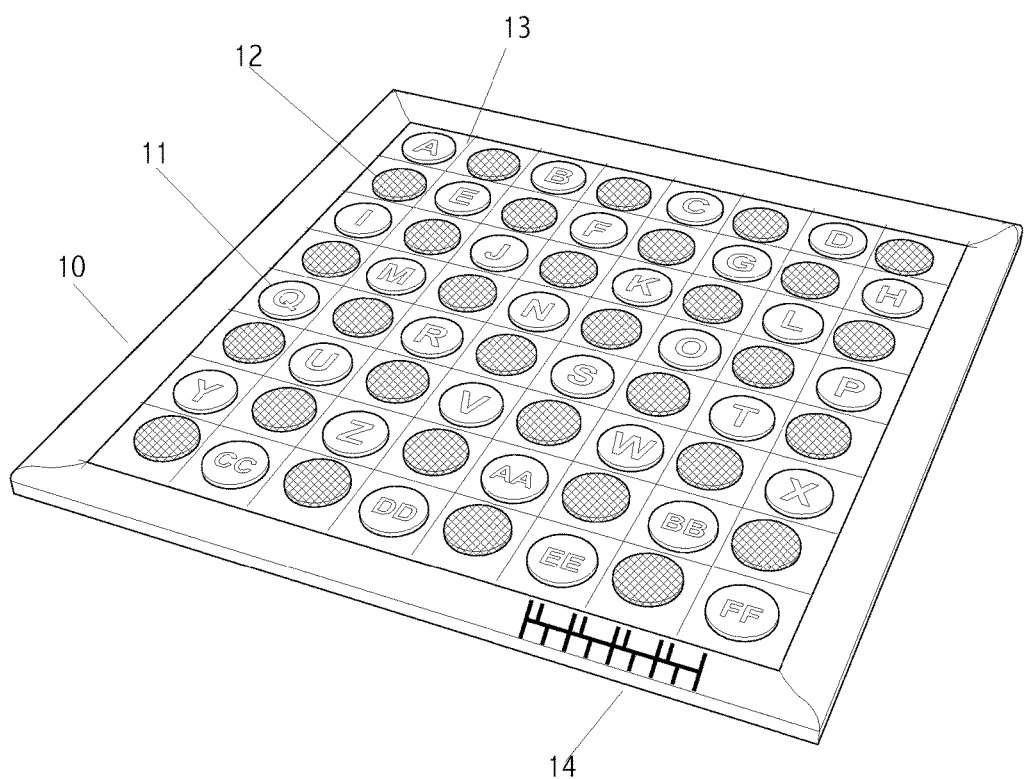
FIG. 1 shows an exemplary pad with urine detection patches and test patches.

Please refer to FIG. 1, which shows an exemplary pad 10 with urine detection patches 12 and test patches, shown with letters. One such test patch is identified by 11, with the letter Q in the Figure. In this embodiment the urine detection patches are arranged in a BAYER pattern, which is similar to a checkerboard. 13 shows gaps or boundaries between the tests patches and urine detection patches. Embodiments of the invention include a test pad comprising a strip or array of multiple test patches. The patches themselves, and what they test, may be similar to prior art test strip patches and need not be discussed in more detail, here. Compounds and attributes typically tested include: leukocytes, nitrite, urobilinogen, protein, pH, hemoglobin, specific gravity, ketone, bilirubin, and glucose.

The pad 10 may be rectangular or another shape. It is typically flat and should be secured in a cage in a known location via adhesive on the back or via alignment pins, snaps, magnets, static electricity or other methods. The pad in the embodiment in this Figure has a chew-proof perimeter, and a machine-readable identification code 14. This code may be for a serial number or lot number.

Figure 8:
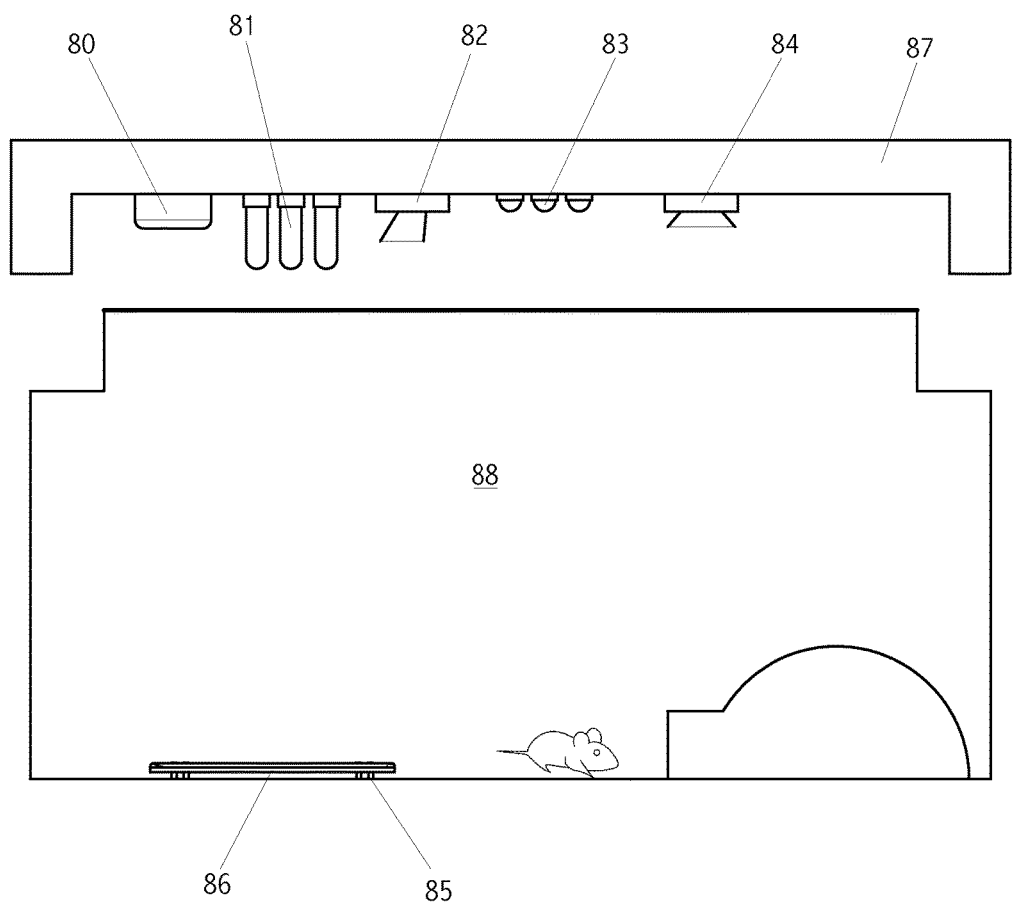
FIG. 8 shows an exemplary animal cage with a test pad, lights and cameras.

As the animals in the cage move around they periodically urinate. When such urination occurs over the test pad the test pad collects the urine and distributes it to one or more test patches in the test pad. One or more video cameras in or proximal to the cage perform two functions. First, they identify that fresh urine is on the test pad, and second, they read the colors of the test patches after the appropriate time delays. Two or more separate cameras may be used for this purpose, or only one camera. Such cameras are shown in FIG. 8. For convenience, we refer to either one or a plurality of cameras as "cameras."

It is important to know the identity of the mouse that produced the urine. We refer to this mouse as the "test mouse." There are numerous methods of mouse identification that need not be detailed here. The cameras that identify and read the test patches on the test pad may also be part of a mouse identification system. RFID may be used. Tattoos, such as machine-readable markings on the mouse's tail may be used.

The test pad comprises multiple test patches in a line, or a grid, or in another arrangement. We refer to the arrangement as an array without limitation to the exact physical pattern of the test patches, unless so specified. Ideally, many patches are used in one pad, including multiple patches that perform the same test. The test pad is typically sufficiently large such that a single urination will saturate, and thus use up, only a subset of the total patches. In this way, the test pad is suitable for multiple urine measurements, including likely measurements from different mice in the cage.

To do this the pad must first distribute a puddle of urine to as many different test patches, or types of test patches, as possible. It must also limit the boundaries of the urine puddle so that the remaining dry patches are available for future measurements.

We refer to the results of a single patch on a single pad as a "test." We refer to an aggregate of one or more tests from a single mouse urination as a "measurement."

The pad must also have a rapid and clear indication of the presence of urine. Positive indication by a "urine presence indicator" starts the timer for the reading of the test patches.

The urine presence indicator may be one of the tests patches or may be a separate indictor. One such suitable indicator is a water damage indicator that changes color when wet. Such sensors are well known in the art. Another such suitable indicator is a specific gravity test patch. These are known in the art and described in more detail, below. Another such suitable indicator is Bromothymol blue.

The urine detection patches perform three functions. First, they start the clock for reading the color of the test patches. Second, they identify which test patches are freshly saturated with urine. Third, they identify which patches are completely dry and may be used for future tests.

In one arrangement, the urine presence indicators are arranged in a checkerboard or BAYER pattern with the test patches, as shown in FIG. 1. This arrangement may be an orthogonal grid or a hexagonal grid or another pattern. If a test patch is completely surrounded by indicators of fresh urine, that test patch may read as part of a measurement. If a test patch is partially surrounded by indicators of fresh urine, it may or may not have sufficient urine present for a valid test, and typically will not be part of a measurement. If a test patch is fully or partially surrounded by indicators of fresh urine it is likely not suitable for future tests.

Embodiments of this invention determine, by using the cameras, the state of test patches with respect to being surrounded by indications of fresh urine and track patch state so that multiple measurements may be taken from a single test pad.

Reading test patches involves both time and color. The test patch must be read in a fairly narrow window of time from first contact with urine. Such time-to-read may be from 20 seconds to 3 minutes, test patch type dependent. Such time-to-read should ideally be accurate, such as within a second or two. In practice, a timing error of 5% to 20% may be acceptable. Typically, different patch types must be read at different times.

Figure 2:
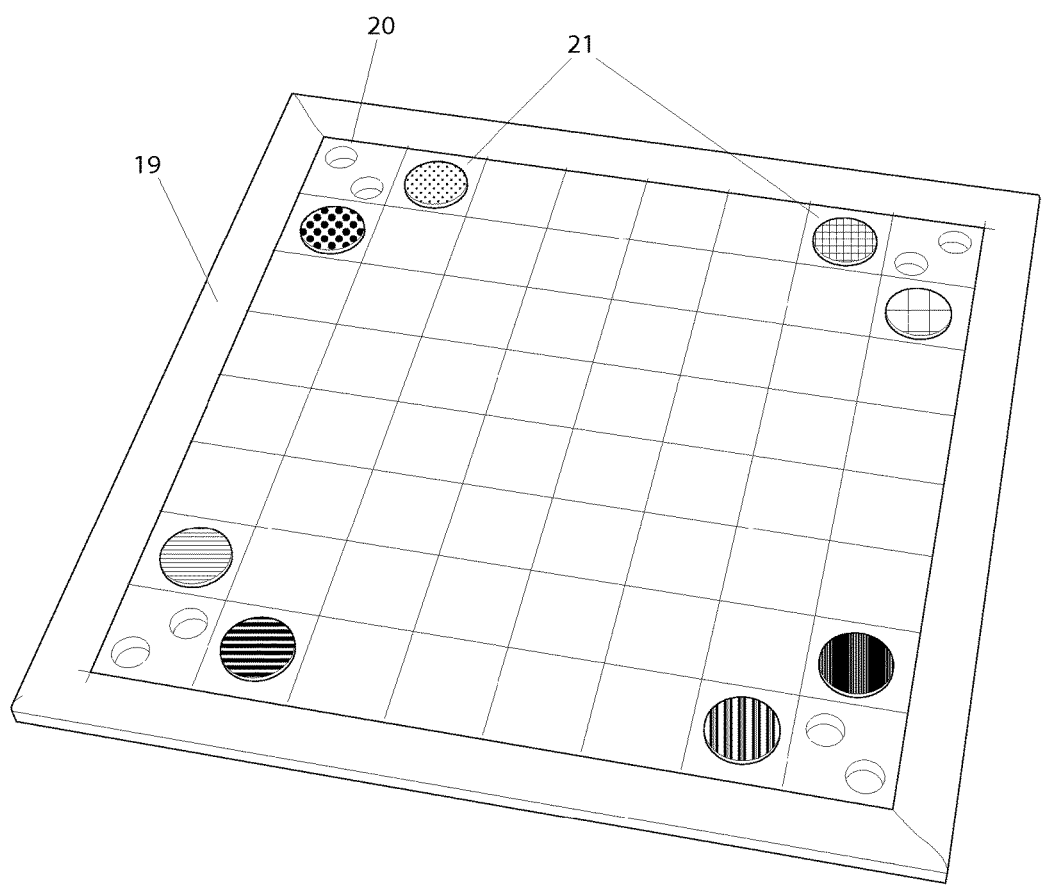
FIG. 2 shows a pad with exemplarily alignment holes, color reference patches, and an ID code.

Please refer to FIG. 2. The color changes of test patches to provide a quantitative test result may be subtle. Therefore, if a camera is used, it is critical that color reference spots be provided. Ideally, these are on each test pad, although they might be separate. For example, a color reference ring or strip might be used around or next to a pad. The color calibration spots should be more than simple RGB or CYMK samples. They should ideally include the same or a subset of the reference colors typically provided with prior art urine test strips, such as on a container of such strips. In this way, video-processing software may also use "the closest match" method of determining the quantitative test value, similar to the way that a human does when manually reading a urine test strip.

Such color reference may be anywhere on the test pad. It may be convenient to place them around the perimeter. They may be elevated so as to minimize the chances that urine or detritus covers them. For convenience we refer to any such spots as "color reference" spots. They may be used for color calibration in either white light, IR light, or both. FIG. 2 shows eight such color reference spots, each with a different pattern. Two such color reference spots are identified as 21. The perimeter of the pad is shown as 19. 20 shows alignment holes in the corners of the test pad. In one embodiment these holes fit over corresponding pins on the cage floor to both align the pad to a known location and orientation, and to secure the pad and keep the animals in the cage from pushing it around. Ideally, the alignment elements permit only a single orientation. Such elements might be snaps, magnets, pins, and the like.

Ideally, white light is used to read the test pad and the color reference spots. However, the natural activity period for mice is nocturnal, in the dark. Infrared (IR) illumination and IR cameras may be used to observe mouse activity in the darkness. However, reading color reference spots with IR light is challenging, although possible.

Thus, in one embodiment, detection of fresh urine is done using IR light and an IR camera, while reading of test patches is done using white light and a color camera.

In one embodiment, the white light is turned on for a brief time during or after the time-to-read delay, and then turned off again.

In yet another embodiment, the white light to illuminate the test pad has a narrow illumination angle focused on the test pad such that the amount of light falling on the mouse or mice in the cage is minimal.

Figure 3:
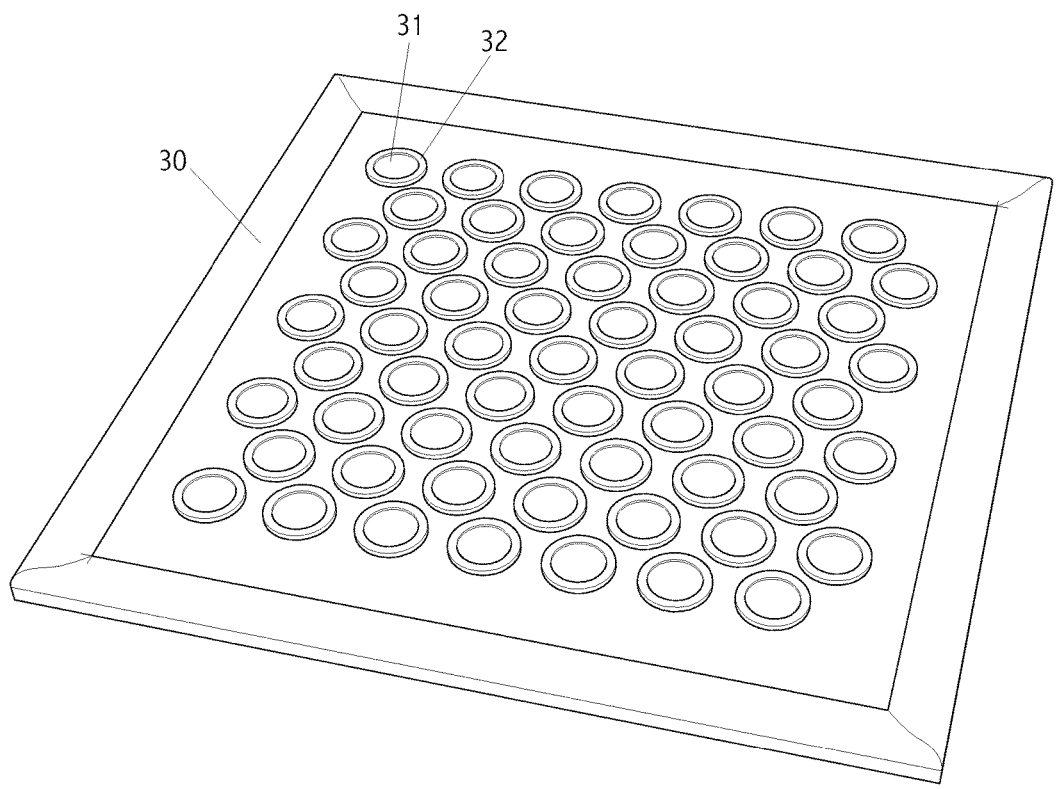
FIG. 3 shows an alternative arrangement of urine detection rings and test patches.

FIG. 3 shows a portion of an alternative arrangement of test patches and urine detection patches. Here, each test patch is surrounded by a urine detection patch, which may be in the shape of donut, as shown, or another shape. 30 identifies the pad. 31 is one typical test patch. 32 is the urine detection patch around the test patch 31. In this Figure, the patches are arranged in a hexagonal pattern, but other patterns, arrays, grids or arrangements may be used, including non-repeating arrangements. Typically, the test patches and urine detection patches are separated so that urine does not readily flow between them, creating clearly defined boundaries of a urine puddle. Such boundaries are discussed more, below. However, a group of test patches may be within a single defined region, cell or well, in which case they may touch, as ideally they are all saturated or all dry.

Figure 4:
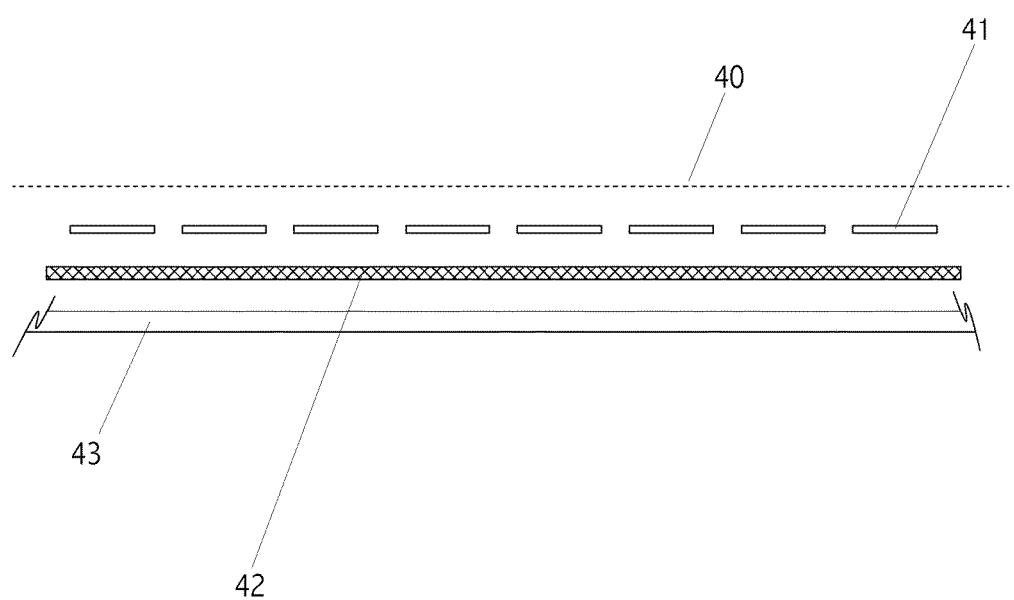
FIG. 4 shows an exemplary arrangement of layers in a cross-section.

Please refer to FIG. 4, which shows one embodiment of layers in the pad in cross-section. 43 is a water-proof substrate layer. Above that is 42, the wicking layer. Above that are the test patches, 41. An optional top protection layer, 40 is shown. This may be a transparent sheet with holes. The urine rapidly penetrates the holes to the test patches and the wicking layer. The wicking layer distributes a puddle of urine evenly to a group of test patches. The test patches may be read through the protection layer. The wicking layer 42 may be integrated with the test patch layer. For example, the wicking layer may be paper on which the test patches are applied or printed. Note that in this embodiment gaps or non-wicking barriers must be provided on this layer to avoid or minimize excessive spreading of the urine pool.

In one embodiment the wicking layer, which may be part of the test patch layer, has portions of the layer, which may be thought of as "fuzz," that penetrate into or through holes in the protection layer. Such entry or penetration assists in moving urine from above the protection layer into the rest of the wicking layer and from there to the test patches. Such penetration by the wicking layer may be achieved by squeezing or pressing (by a press or pinch rollers, for example) the pad during manufacture.

In another embodiment the holes in the protection layer are treated with a substance, treatment or coating that makes the holes hydrophilic. In this way urine moves easily through the hole.

It is desirable for fresh urine to rapidly saturate a test patch. However, the boundary of the urine should be clearly defined, so that test patches beyond the boundary are not contaminated with trace quantities of previous urine. Thus, the wicking layer should not be an absorbent, such as cellulose paper. Also, it must be neutral and not interact with the urine as that might change the characteristics that are measured by the test patches. One such suitable material is fine fiberglass. Another such material is a porous fabric of non-porous plastic fibers, such as polyester or rayon. The surface of the fibers should be sufficiently hydrophilic such that the urine flows through the spaces in the fabric, yet sufficiently hydrophobic that the puddle of urine does not expand beyond a well-defined boundary. Polyamides may be used. Surface treatment to make surfaces more or less hydrophilic/hydrophobic are well known in the art. The fabric may be a non-porous sheet with grooves, where the urine flows in the grooves but does not penetrate the sheet.

Since test patches are typically placed on a porous material, such as cellulose paper, the wicking layer of the test pad may be below the test layer. However, the test patches, if on their own porous material, must be physically isolated from each other so that urine does not migrate through the test patch layer. This isolation is shown as gaps between the test patches 41 in FIG. 4.

In one embodiment a plurality of regions are created where the region has a substance, treatment or coating that is hydrophilic so that urine spreads out across the region. In one embodiment, barriers or lines between such regions have a substance, treatment or coating that is hydrophobic so as to limit urine puddles to the one or more regions. The purpose of such hydrophilic and hydrophobic applications or treatments (which may be used singly or together) is create effective "wells" that trap urine into one or more well-defined regions. The goal is that as many test patches on the pad as possible are either fully saturated with urine so as to provide a valid test result or remain completely dry so that they are usable for future tests.

An optional top protection layer may have an exemplary hole pattern of 0.2 mm holes on a 1 mm or 0.5 mm spacing. This layer should be transparent to permit video reading of the test patches below. A suitable hole spacing in the protection layer is 0.3 to 2.0 mm. A suitable hole diameter is 0.1 to 0.8 mm. A purpose of the holes is to be small enough that mice cannot get their teeth into them, to prevent chewing of the pad or its elements. Hole size may thus need to vary with the type and age of the rodents. Alternative elements and methods that allow urine to pass through the protection layer may be used. Holes should be large enough to permit urine to flow through quickly enough to avoid an overly large puddle, or a poorly formed puddle boundary, at the test layer. The surface of the protection layer may be hydrophobic to keep urine in a defined puddle, such as by the material itself or a coating. The holes of the protection layer may be hydrophilic to permit rapid penetration of urine. Alternatively, portions of the wicking layer may penetrate upward into or through the holes. One method to accomplish this is by pressure forming the wicking layer with the protection layer.

Figure 5:
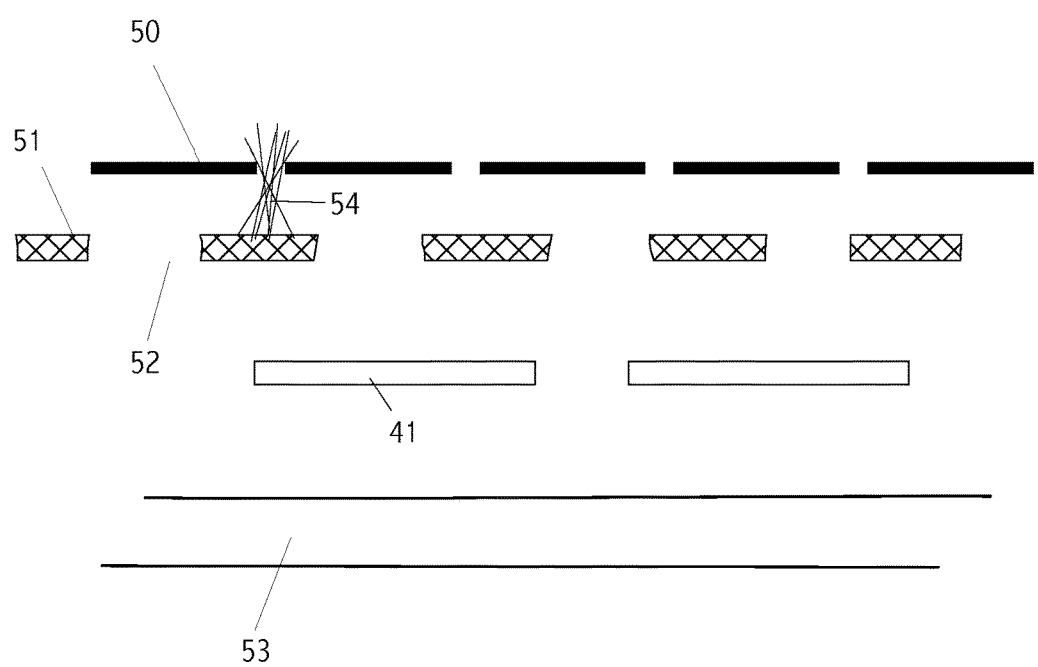
FIG. 5 shows an alternative arrangement of layers in a cross-section.

Please refer to FIG. 5, which shows an alternative embodiment of layers, in cross-section. The non-porous substrate is on the bottom, 53. This layer protects the test patch layer and wicking layer from contamination from below, and may provide mechanical strength for the pad. It also prevents urine in the pad from leaking through the bottom. Above the substrate, in this Figure, are the test patches, layer 41. Above the test patches is the wicking layer, 51. Because the wicking layer in this embodiment is above the test patch layer, it must have openings through which the test patches may be viewed. One such opening is shown as 52. An optional transparent protection layer with holes is shown, 50.

In one embodiment, portions of the wicking layer 51 stick in or through the holes in the protection layer 50. This penetration may be thought of as "fuzz." Such penetration is shown as 54. Although this fuzz is shown in only one location in this Figure, typically it would be in a plurality of, or all holes. Although the Figure shows a gap between the wicking layer 51 and the protection layer 50 for clarity, in practice this gap is likely minimal or missing. Such penetration of the wicking layer into or through the protection layer is expressly claimed.

Embodiments of this invention include construction of test pads from various layers, in various orders.

Figure 6:
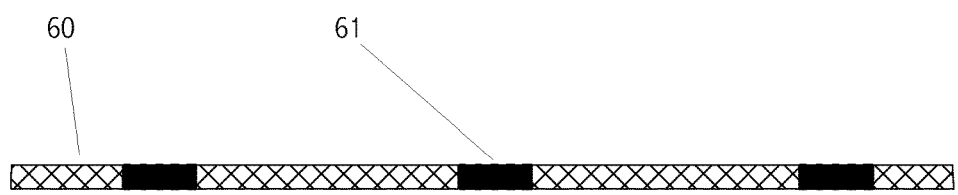
FIG. 6 shows an exemplary wicking layer with urine boundaries, in cross-section.

Looking now at FIG. 6, we see an embodiment with urine wicking boundary lines in the wicking layer, in cross-section. The wicking layer is shown as 60. One such wicking boundary is shown as 61. Such boundary lines may be created by melting the wicking layer, for example if polyester fibers or polyamide are used in the wicking layer. Alternatively, a hardening and filling material, such a wax or glue, may be applied in lines. Alternatively, a boundary line may be created using a hydrophobic substance or treatment in or on the wicking layer. Ideally, regions, wells, or cells are created by the wicking layer boundary lines such that urine saturates the test patches within the region and does not flow, or flows minimally, out of the region, maintaining adjacent or nearby test patches dry and available for future tests.

Figure 7:
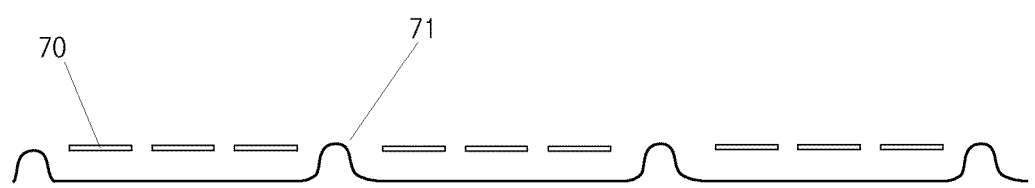
FIG. 7 shows an exemplary substrate layer with urine wells.

Please refer to FIG. 7. Yet another embodiment uses defined wells to contain regions or puddles of urine. This figure shows a cross-section of three wells. Each well might comprise one or more test patches and one or more urine presence indicators. For example, a well might hold two test patches and two urine presence indicators. A wicking layer is used within the well to distribute urine across the well. The well has walls, or barriers, which block urine flow between wells, unless the quantity of urine is such that it floods over the tops of the walls. In this embodiment, the wicking layer within the wells may be porous, such as cellulose paper. The well borders may be hydrophobic ridges. This Figure shows well walls created by forming the substrate layer in to ridges, 71. Each well in this Figure comprises multiple test patches, 70, and at least one urine detection patch, not shown.

In one embodiment, urine well ridges are formed from the same monolithic sheet as the substrate of the test pad. For example, the substrate may be pressed, heat molded, vacuum formed or injection molded to create the ridges, thus forming wells.

As a test pad is used in a cage, various urinations cause the test patches to be used. Each test patch is typically available for only a single use.

FIG. 8 shows a typical use and embodiment in a mouse cage. 88 is the mouse cage. 86 is a test pad, with alignment and retention elements shown as 85. White LEDs are shown as 81. IR LEDs are shown as 83. A color camera is shown as 82. An IR camera is shown as 84. 80 shows a device to provide a stimulus to the animals in the cage, such as a noise, scent, or light. UV LEDs may be used in some embodiments; they are not shown in the Figure. The white light from LEDs 81 may be narrowly focused just to the pad, 86. In one embodiment the field of view and the focus of the color camera, 82, looks only at the pad; while the IR camera, 84, has a field of view of the entire cage. However, both cameras may be combined in one embodiment. The electronics: 80, 81, 82, 83, 84, and other electronics for the cage, not shown, are mounted in or on a "slab," 87, that resides on the top of the cage, as shown. Other arrangements of the electronic components are used in other embodiments.

Mouse identification may occur at only certain locations within the cage or at certain times or mouse positions. Therefore, embodiments of this invention use the cameras to track the test mouse between the location of urination and an identification reading location. Note that the mouse identification may occur either prior to urination or after.

In one embodiment, white light to illuminate the test pad is turned on only if there are no mice within the illumination area of the white light. While this might cause a test measurement to be unavailable, the mice in the cage are not harmed or stressed by the use of white light during their natural period of darkness.

Determining the closest match of a test patch to color reference spots may be accomplished by various methods. One method chooses the shortest vector in a 3D color space model, where each vector for comparison is between the test patch and each of the set of applicable color reference spots. A preferred method is to use a weighted vector on a vector in only on axis or in one place of a 3D color space model. For example, if one test patch changes luminosity, but not hue, it would be appropriate to compare vector length only in the luminosity axis. Similarly if one test patch changes hue only, or saturation only, it would be appropriate to compare vector length only on those axes. One way to determine an optimum axis, within a 3D color space model, is to analyze all of the color reference spots for one test patch. The choose the best line, either straight or curved, within a 3D color space model, that passes through all of those color reference dots. Then a minimum vector length along this line is used for selecting the closest color reference spot, and also may be used for interpolation between color reference spots. Camera readings and computations are best done in real time, each time new readings of test patches are taken. Illumination sources and camera settings are prone to change. Therefore, current readings are likely to be more accurate than an earlier calibration. The methods and method steps of this paragraph are specifically claimed as methods and method steps of embodiments.

Figure 9:
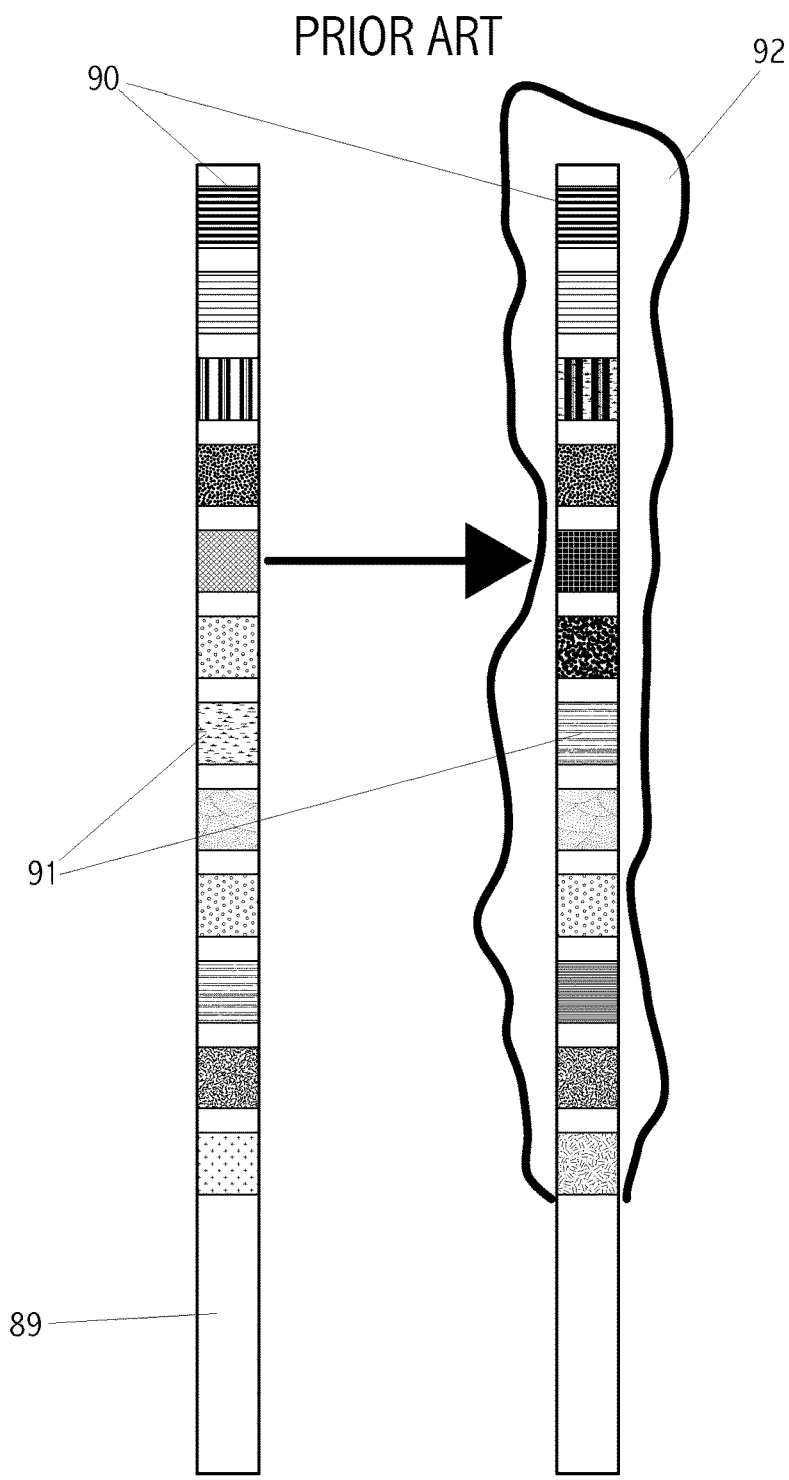
FIG. 9 shows prior art test strip.

FIG. 9 shows prior art. Here 89 is a common urine test strip with 12 test patches shown. The strip in the left column is dry. In the right column, in a puddle of urine, 92, the test patches are activated and may be read. In this Figure, wet test patch 90 has not changed from its dry color. Test patch 91 has changed.

Rodents have difficulty gaining purchase with their teeth on surfaces with a curvature that exceeds a predetermined radius, where that radius threshold is dependent on the size of the rodent, including species, strain, and age. Such thresholds are in the range of 0.2 mm to 4 cm. Another range is 0.5 to 1.5 cm. Therefore, in some embodiments the pad has no exterior portions with a radius or thickness than this predetermined radius threshold. For example, the corners of the pad may be rounded. The shape of the pad may be a "stage," where the edge of the stage also has a minimum curvature. Such shape limitations are expressly claimed.

In one embodiment the pad has "feet," or a "wall," or some other element to raise the pad above the floor of the cage to the height of or higher than the bedding in the cage. Such a height minimizes the amount of bedding that gets on the surface of the pad. In one embodiment, such feet also secure the pad to the cage floor and also provide for a predetermined location and alignment within the cage.

In one embodiment the described "stage" comprises a slot through which a pad may be inserted. In this embodiment, the stage may provide either the substrate layer for support, or the protection layer, or both.

In one embodiment the pad may be placed on or built into the top of another apparatus in a cage, such as a scale. Adhesive, such as an adhesive strip, may be in the center of the pad or around the perimeter. The pad may fit in a recess in the top of the scale or other apparatus.

In one embodiment the pad has one or more regions treated with a scent or protein to encourage visitation by a rodent. In one embodiment the scent of protein is gender specific to encourage or discourage one gender over another vendor from visiting or staying away from the pad. Thus, it is possible (and claimed) to manufacture or configure pads that are "male urine test pads," or "female urine test pads." Such scents and proteins are well known in the art. Pads may have one or more removable covers, such as tape, that exposes the scent or proteins so that a pad may be rapidly configured in the field. Alternatively, a "scratch and sniff" coating may be used, such as known in the art.

In alternative embodiments urine is detected, or the scope of a urine pool is detected, or both, by the use of UV illuminators and camera(s) configure to respond to the fluorescent wavelength(s) of urine. For example, excitation wavelength may be 290 to 390 nm, such as 370 nm. Peak fluorescent wavelength may be 400 to 500 nm, such as 425 or 440 nm. While a portion of the fluorescent light may be outside of "visible" range, a camera may have sensitivity within the fluorescent wavelength spectra. The UV illuminators, typically UV LEDs, are ideally focused just on the test pad. They may be turned on only when a rodent is present, or just after a rodent leaves the test pad.

In one embodiment the urine test patch comprises a specific gravity test patch as described (from Wikipedia.org, retrieved on 2015 Sep. 29):

> The specific gravity of urine is a measure of the density of the substances dissolved in it and it depends on the number of dissolved particles and their mass. The molecules with the greatest mass contribute more to the measure of specific gravity than smaller molecules. The measurement of specific gravity should not be confused with the measurement of osmotic concentration, which is more related to the number of particles than with their mass. The urine test strip test for specific gravity is based on the change in dissociation constant (pKa) of an anionic polyelectrolyte (poly-(methyl vinyl ether/maleic anhydride)) in an alkali medium that is ionised and releases hydrogen ions in proportion to the number of cations present in the solution. The greater the cation concentration of the urine the more hydrogen ions are released, thereby reducing the pH. The pad also includes Bromothymol blue, which measures this change in pH. It should be remembered that the test strip only measures cation concentration, it is therefore possible that urine with a high concentration of non-ionic solutes (such as glucose or urea) or with high molecular weight compounds (such as the media used to provide radiographic contrast) will yield a result that will be erroneously lower that that measured by densitometry. The colors vary from dark blue with a reading of 1.000 to yellow for a reading of 1.030.
>
> 1) In an alkaline medium
>
> 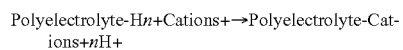
>
> 2) In an alkaline medium
>
> 
>
> Elevated protein concentrations produce slightly elevated specific density results as a consequence of the indicator's protein error, in addition, samples with a pH above 6.5 give lower readings as a result of the indicator's bias. For this reason the manufacturers recommend that 5 units are added to the specific gravity reading when the pH is greater than 6.5.

Embodiments of this invention explicitly include all combinations and sub-combinations of all features, elements and limitation of all claims. Embodiments of this invention explicitly include all combinations and sub-combinations of all features, elements, examples, embodiments, tables, values, ranges, and drawings in the specification and drawings. Embodiments of this invention explicitly include devices and systems to implement any combination of all methods described in the claims, specification and drawings. Embodiments of the methods of invention explicitly include all combinations of dependent method claim steps, in any functional order. Embodiments of the methods of invention explicitly include, when referencing any device claim, a substitution thereof to any and all other device claims, including all combinations of elements in device claims.

Definitions

The term, "pad," as used herein is a general flat sheet comprising one or more layers. The shape may vary but ideally is rectangular. Different portions of a pad may be raised or recessed. The pad may comprise a perimeter, which may be a lip and may be a different material. The pad may have aligning element(s) used to position the pad in a location with mating element(s) that are not part of the pad. The pad may have securing element(s) to hold the pad in position.

Communication—may be electromagnetic, optical or audio. Audio comprises sub-audio and ultrasonic audio.

Gantry—any support for a linear track, including the track itself, or an open support or closed support. May include a rectangular enclosure or a system adapted to be secured in an existing support structure (such as a bench or fume hood).

IR LED—An IR LED is one in which its spectrum peaks or is predominantly in the infrared spectrum, as normally defined with respect to IR LEDs and IR cameras. Note there may be some overlap between the "IR spectrum" and the "visible light spectrum."

Pad—A pad is a general flat sheet comprising one or more layers. The shape may vary but ideally is rectangular. Different portions of a pad may be raised or recessed. The pad may comprise a perimeter, which may be a lip and may be a different material. The pad may have aligning element(s) used to position the pad in a location with mating element(s) that are not part of the pad. The pad may have securing element(s) to hold the pad in position.

Pathogen-free—means the population of microbes, including but not limited to bacteria, viruses, prions and toxins, relevant to the experiment, are sufficiently reduced to meet the needs of the study, or to not impact the health, performance or behavior of the target animal population or of the workers.

Primary cage or home cage—the cage in which an animal spends more time than any other cage. Of note, there is a related term of art: "home cage." The definition of primary cage is, in some embodiments, the home cage. An aspect of home cage/primary cage deals with the fungibility of the actual cage itself. Each time a cage is changed, the physical cage is generally either disposed or removed for washing, and replaced by a clean cage. The new physical cage is considered the same primary cage. A primary cage may sometimes be distinguished from a non-primary cage by the purpose of the cage. For example, a home cage may be for living in, as compared to a experimental cage to which the animal is transferred that is equipped or located for one or more particular experiments for the applicable study.

The primary cage is different from special purpose, behavioral-measurement, behavioral-detection, or behavioral-observation cages that are generally used for only a short time for the duration of a particular test due to cost and mindset.

Sealed enclosure—an enclosure sealed against pathogens that impact or alter study results, or alter the credibility or repeatability of study results, entering or leaving the enclosure.

Sensor—may or may not include the use of local or remote processors, and may or may not include local or remote software executing on the local or remote processors. Sensors may or may not communicate over a network. Multiple sensors may or may not include common elements.

Set—one or more, unless stated otherwise.

Subset—one or more of a set, including all elements of the set, unless stated otherwise.

Sterile—pathogen-free.

Transparent—for a pad cover layer the term transparent also includes translucent.

Visible light—Free of visible light mans the ambient light is sufficiently low and in a spectrum such that the animal's physiological state and behavior are consistent with its natural physiological state and behavior at night.

White light—Light with wavelengths across the visible spectrum that is suitable for seeing color using a conventional color camera, as conventionally defined in the art. Note that white light may include some wavelengths outside of the visible spectrum.

Ideal, Ideally, Optimum and Preferred—Use of the words, "ideal," "ideally," "optimum," "optimum," "should" and "preferred," when used in the context of describing this invention, refer specifically a best mode for one or more embodiments for one or more applications of this invention. Such best modes are non-limiting, and may not be the best mode for all embodiments, applications, or implementation technologies, as one trained in the art will appreciate.

May, Could, Option, Mode, Alternative and Feature—Use of the words, "may," "could," "can," "option," "optional," "mode," "alternative," "typical," "ideal," and "feature," when used in the context of describing this invention, refer specifically to various embodiments of this invention. Described benefits refer only to those embodiments that provide that benefit. All descriptions herein are non-limiting, as one trained in the art appreciates.

What is claimed is:

1. A device for measuring attributes of urine comprising:
a pad comprising a test patch layer comprising:
a plurality of different urine test patches, each different urine test patch comprising one or more respective urine test chemicals that change color responsive to a respective urine attribute;
a plurality of urine detection patches, wherein the urine detection patches are different from any urine test patch, and wherein each urine detection patch comprises one or more chemicals that change color responsive to presence of urine;
wherein each different urine test patch is at least partially surrounded by one or more of the urine detection patches;
the urine detection patches and urine test patches are arranged in a BAYER pattern, wherein the urine detection patches are arranged in a checkerboard pattern within the BAYER pattern and the urine test patches are distributed among the remaining location in the BAYER pattern;
a wicking layer above the test patch layer;

a transparent protection layer with holes, above the wicking layer;

a non-porous substrate below the test patch layer;

wherein the urine detection patches and the urine test patches are on the test patch layer.

2. A device for measuring attributes of urine comprising:

a pad comprising a test patch layer comprising:

a plurality of different urine test patches, each different urine test patch comprising one or more respective urine test chemicals that change color responsive to a respective urine attribute;

a plurality of urine detection patches, wherein the urine detection patches are different from any urine test patch, and wherein each urine detection patch comprises one or more chemicals that change color responsive to presence of urine;

wherein each different urine test patch is at least partially surrounded by one or more of the urine detection patches;

the urine detection patches and urine test patches are arranged in a BAYER pattern, wherein the urine detection patches are arranged in a checkerboard pattern within the BAYER pattern and the urine test patches are distributed among the remaining location in the BAYER pattern;

a protection layer above the test patch layer, transparent or translucent;

comprising holes adapted to pass urine from above the top layer into the test patch layer;

a urine impenetrable substrate layer below the test patch layer.

3. The device of claim 1 wherein:

a color of each detection patch and a color of each test patch layer are viewable through the wicking layer.

4. The device of claim 1 further comprising:

at least one scent region comprising a chemical scent attractive to a single sex of a rodent.

5. The device of claim 1 further comprising:

at least one scent region comprising a chemical scent attractive to a single sex of a rodent.

6. The device of claim 1 further comprising:

well boundaries in the substrate layer comprising previously melted portions of the substrate layer;

wherein wells are defined by the well boundaries;

and wherein the wells are fluidly isolated from each other;

and wherein each well comprises at least one urine detection patch and at least one urine test patch.

7. The device of claim 1 wherein:

portions of the wicking layer protrude into the holes in the transparent protection layer.

\* \* \* \* \*